US010307608B2

(12) United States Patent
Baek et al.

(10) Patent No.: US 10,307,608 B2
(45) Date of Patent: Jun. 4, 2019

(54) AWARENESS GLASSES, CAR MIRROR UNIT, AND DISPLAY APPARATUS CONFIGURED TO INCREASE USER AWARENESS

(71) Applicant: Samsung Display Co., Ltd., Yongin (KR)

(72) Inventors: Jongin Baek, Suwon-si (KR); Haksun Kim, Seoul (KR); WonSang Park, Yongin-si (KR); Mingyeong Jo, Busan (KR)

(73) Assignee: Samsung Display Co., Ltd, Yongin-si (KR)

( * ) Notice: Subject to any disclaimer, the term of this patent is extended or adjusted under 35 U.S.C. 154(b) by 0 days.

(21) Appl. No.: 15/654,897

(22) Filed: Jul. 20, 2017

(65) Prior Publication Data

US 2017/0312541 A1 Nov. 2, 2017

Related U.S. Application Data

(62) Division of application No. 14/516,422, filed on Oct. 16, 2014, now abandoned.

(30) Foreign Application Priority Data

Dec. 30, 2013 (KR) ........................ 10-2013-0167182

(51) Int. Cl.
*A61N 5/06* (2006.01)
*G02B 5/18* (2006.01)
(Continued)

(52) U.S. Cl.
CPC .......... *A61N 5/0618* (2013.01); *B60R 1/1207* (2013.01); *G02B 5/1814* (2013.01);
(Continued)

(58) Field of Classification Search
CPC ................ G02B 27/01; G02B 27/0101; G02B 27/0103; G02B 27/017; G02B 27/0172;
(Continued)

(56) References Cited

U.S. PATENT DOCUMENTS 5,402,109 A 3/1995 Mannik
5,469,143 A 11/1995 Cooper
(Continued)

FOREIGN PATENT DOCUMENTS

BE 1018173 6/2010
BE 1018173 A3 * 6/2010 ........... A61M 21/00
(Continued)

OTHER PUBLICATIONS

English machine translation of BE 1018173 A3.*
(Continued)

*Primary Examiner* — Nicholas R Pasko
(74) *Attorney, Agent, or Firm* — H.C. Park & Associates, PLC

(57) ABSTRACT

A pair of awareness glasses includes a frame, a light source, a driving unit, light guide lenses, and diffraction grating patterns. The light source unit is disposed in the frame. The light source unit is configured to generate light in response to input power. The driving unit is configured to supply the input power. The light guide lenses are configured to guide the light to the eyes of a user. The diffraction grating patterns are formed on surfaces of the light guide lenses. The diffraction grating patterns are configured to diffract and reflect the light to the eyes of the user. The light output from each of the diffraction grating patterns has a peak wavelength between 444 nm and 484 nm.

8 Claims, 13 Drawing Sheets

211
220
221
A1
241

(51) Int. Cl.

| | |
|---|---|
| ***B60R 1/12*** | (2006.01) |
| ***G02B 19/00*** | (2006.01) |
| *G02C 11/04* | (2006.01) |
| *A61M 21/00* | (2006.01) |
| *G02C 7/08* | (2006.01) |

(52) U.S. Cl.
CPC . *G02B 19/0061* (2013.01); *A61M 2021/0044* (2013.01); *A61N 2005/0648* (2013.01); *G02C 7/086* (2013.01); *G02C 11/04* (2013.01)

(58) Field of Classification Search
CPC ........ G02B 2027/0105–2027/013; A61N 5/06; A61N 5/0618; A61N 2005/0647; A61N 2005/0648; G02C 11/04; A61M 2021/0044
USPC .............. 359/13–14, 629–633; 340/575, 576
See application file for complete search history.

(56) References Cited

U.S. PATENT DOCUMENTS

| | | | | | |
|---|---|---|---|---|---|
| 5,982,287 | A | | 11/1999 | Brannen et al. | |
| 6,350,275 | B1 | | 2/2002 | Vreman et al. | |
| 7,204,625 | B2 | * | 4/2007 | Wiemers | B60Q 3/72 362/490 |
| 7,301,465 | B2 | | 11/2007 | Tengshe et al. | |
| 7,944,616 | B2 | | 5/2011 | Mukawa | |
| 8,366,755 | B2 | | 2/2013 | Brainard et al. | |
| 9,599,813 | B1 | * | 3/2017 | Stratton | G02B 27/0101 |
| 2003/0069616 | A1 | | 4/2003 | Skene et al. | |
| 2004/0233060 | A1 | | 11/2004 | Mohri | |
| 2006/0132914 | A1 | * | 6/2006 | Weiss | G02B 5/32 359/462 |
| 2006/0136018 | A1 | | 6/2006 | Lack et al. | |
| 2007/0233207 | A1 | * | 10/2007 | Poirrier | A61M 21/00 607/88 |
| 2007/0268234 | A1 | * | 11/2007 | Wakabayashi | A61M 21/00 345/102 |
| 2008/0106694 | A1 | * | 5/2008 | Blum | G02C 5/143 351/158 |
| 2010/0157400 | A1 | * | 6/2010 | Dimov | G02B 5/188 359/13 |
| 2010/0214559 | A1 | * | 8/2010 | Brainard | A61N 5/0618 356/213 |
| 2010/0220295 | A1 | | 9/2010 | Mukawa et al. | |
| 2010/0253526 | A1 | * | 10/2010 | Szczerba | B60K 28/066 340/576 |
| 2012/0203310 | A1 | | 8/2012 | Pugh et al. | |
| 2013/0278887 | A1 | * | 10/2013 | Legerton | G02C 11/00 351/158 |
| 2013/0304162 | A1 | | 11/2013 | Veres et al. | |
| 2014/0092482 | A1 | * | 4/2014 | Dubroca | G02B 27/0101 359/633 |
| 2014/0184775 | A1 | * | 7/2014 | Drake | A61B 3/14 348/78 |
| 2016/0187673 | A1 | | 6/2016 | Maitre et al. | |

FOREIGN PATENT DOCUMENTS

| | | | | | |
|---|---|---|---|---|---|
| BE | 1018173 | A3 | * | 6/2010 | A61M 21/00 |
| JP | 2008-027044 | | | 2/2008 | |
| JP | 2008027044 | A | * | 2/2008 | |
| JP | 2008027044 | A | * | 2/2008 | |
| KR | 10-1999-0009019 | | | 2/1999 | |
| KR | 10-1999-0084391 | | | 12/1999 | |
| KR | 10-0296534 | | | 11/2001 | |
| KR | 10-0760493 | | | 9/2007 | |
| KR | 10-0940004 | | | 2/2010 | |
| KR | 10-1021039 | | | 3/2011 | |
| KR | 10-1128635 | | | 3/2012 | |

OTHER PUBLICATIONS

English machine translation of JP 2008027044 A.*
English machine translation of BE 1018173 A3 (Year: 2010).*
English machine translation of JP 2008027044 A (Year: 2008).*
Final Office Action dated May 30, 2017, in U.S. Appl. No. 14/516,422.
Non-Final Office Action dated Feb. 1, 2017, in U.S. Appl. No. 14/516,422.
Final Office Action dated Sep. 16, 2016, in U.S. Appl. No. 14/516,422.
Non-Final Office Action dated May 18, 2016, in U.S. Appl. No. 14/516,422.
Wright et al., “Light emitting diodes can be used to phase delay the melatonin rhythm,” Journal of Pineal Research, Dec. 2001, pp. 350-355, vol. 31, No. 4, Munksgaard.
Brainard et al., “Action Spectrum for Melatonin Regulation in Humans: Evidence for a Novel Circadian Photoreceptor,” The Journal of Neuroscience, Aug. 15, 2001, pp. 6405-6412, vol. 21, No. 16, Society for Neuroscience.

* cited by examiner

AWARENESS GLASSES, CAR MIRROR UNIT, AND DISPLAY APPARATUS CONFIGURED TO INCREASE USER AWARENESS

CROSS-REFERENCE TO RELATED APPLICATION

This application is a Divisional of U.S. patent application Ser. No. 14/516,422, filed Oct. 16, 2014, and claims priority from and the benefit of Korean Patent Application No. 10-2013-0167182, filed Dec. 30, 2013, each of which is incorporated by reference for all purposes as if set forth herein.

BACKGROUND

Field

Exemplary embodiments relate to awareness glasses, a car mirror unit, and a display apparatus, and, more particularly, to awareness glasses with an awareness feature, a car mirror unit with an awareness feature, and a display apparatus with an awareness feature.

Discussion

Cars include various systems and features to protect passengers. For instance, a protecting system might provide a driver with a comfortable driving condition, but may also cause an overly simple and boring experience. This may lead to the driver becoming drowsy or even falling asleep. As such, devices are being developed to prevent (or otherwise reduce) drowsy driving. For example, a device may recognize and detect that a driver is becoming sleepy and provide an alert (or other stimulus) to awaken the driver. Also, an awareness device to provide an awareness effect with a user to improve learning efficiency and/or productivity may be useful.

The above information disclosed in this Background section is only for enhancement of understanding of the background of the inventive concept, and, therefore, it may contain information that does not form the prior art that is already known in this country to a person of ordinary skill in the art.

SUMMARY

Exemplary embodiments provide awareness features in awareness glasses, car mirror units, and display devices.

Additional aspects will be set forth in the detailed description which follows, and, in part, will be apparent from the disclosure, or may be learned by practice of the inventive concept.

According to exemplary embodiments, a pair of awareness glasses includes a frame, a light source, a driving unit, light guide lenses, and diffraction grating patterns. The light source unit is disposed in the frame. The light source unit is configured to generate light in response to input power. The driving unit is configured to supply the input power. The light guide lenses are configured to guide the light to eyes of a user. The diffraction grating patterns are formed on surfaces of the light guide lenses. The diffraction grating patterns are configured to diffract and reflect the light to the eyes of the user. The light output from each of the diffraction grating patterns has a peak wavelength between 444 nm and 484 nm.

According to exemplary embodiments, a car mirror unit includes a light source unit, a driving unit, a light guide mirror, and a diffraction grating pattern. The light source unit is configured to generate light in response to a driving voltage. The driving unit is configured to supply the driving voltage to the light source unit. The light guide mirror is configured to guide the light. The light guide mirror is disposed in front of a driver. The diffraction grating pattern is formed on a surface of the light guide mirror. The diffraction grating pattern is configured to diffract and reflect the light to the eyes of the driver. The light output from the diffraction grating pattern has a peak wavelength between 444 nm and 484 nm.

According to exemplary embodiments, a display apparatus includes a display unit and an awareness optical unit. The display unit is configured to display an image. The awareness optical unit is disposed on the display unit. The awareness optical unit is configured to provide a user with light in a peak wavelength ranging from 444 nm to 484 nm. The awareness optical unit includes a light source unit configured to generate light and an awareness plate disposed on the display unit to guide the light from the light source unit. The awareness plate includes a diffraction grating pattern formed on a surface of the awareness plate. The diffraction grating pattern is configured to diffract and reflect the guided light to the eyes of the user.

The foregoing general description and the following detailed description are exemplary and explanatory and are intended to provide further explanation of the claimed subject matter.

BRIEF DESCRIPTION OF THE DRAWINGS

The accompanying drawings, which are included to provide a further understanding of the inventive concept, and are incorporated in and constitute a part of this specification, illustrate exemplary embodiments of the inventive concept, and, together with the description, serve to explain principles of the inventive concept.

DETAILED DESCRIPTION OF THE ILLUSTRATED EMBODIMENTS

Figure 1:
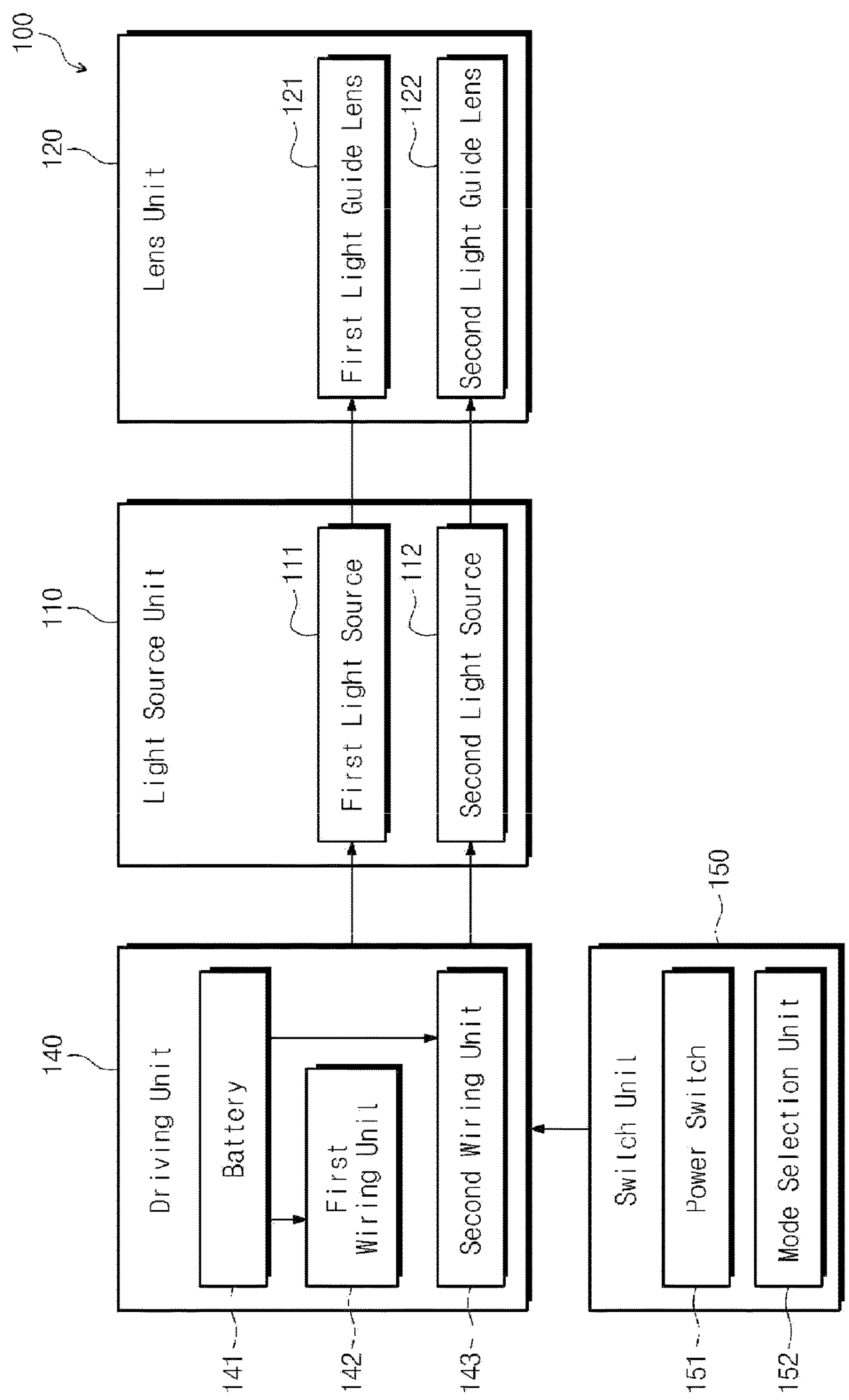
FIG. 1 is a block diagram of a pair of awareness glasses, according to exemplary embodiments.

In the following description, for the purposes of explanation, numerous specific details are set forth in order to provide a thorough understanding of various exemplary embodiments. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments.

In the accompanying figures, the size and relative sizes of layers, films, panels, regions, etc., may be exaggerated for clarity and descriptive purposes. Also, like reference numerals denote like elements.

When an element or layer is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. Like numbers refer to like elements throughout. As used herein, the term "and/or" includes any and all combinations of one or more of the associated listed items.

Although the terms first, second, etc. may be used herein to describe various elements, components, regions, layers, and/or sections, these elements, components, regions, layers, and/or sections should not be limited by these terms. These terms are used to distinguish one element, component, region, layer, and/or section from another element, component, region, layer, and/or section. Thus, a first element, component, region, layer, and/or section discussed below could be termed a second element, component, region, layer, and/or section without departing from the teachings of the present disclosure.

Spatially relative terms, such as "beneath," "below," "lower," "above," "upper," and the like, may be used herein for descriptive purposes, and, thereby, to describe one element or feature's relationship to another element(s) or feature(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof.

Various exemplary embodiments are described herein with reference to sectional illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not be construed as limited to the particular illustrated shapes of regions, but are to include deviations in shapes that result from, for instance, manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the drawings are schematic in nature and their shapes are not intended to illustrate the actual shape of a region of a device and are not intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and will not be interpreted in an idealized or overly formal sense, unless expressly so defined herein.

Figure 2:
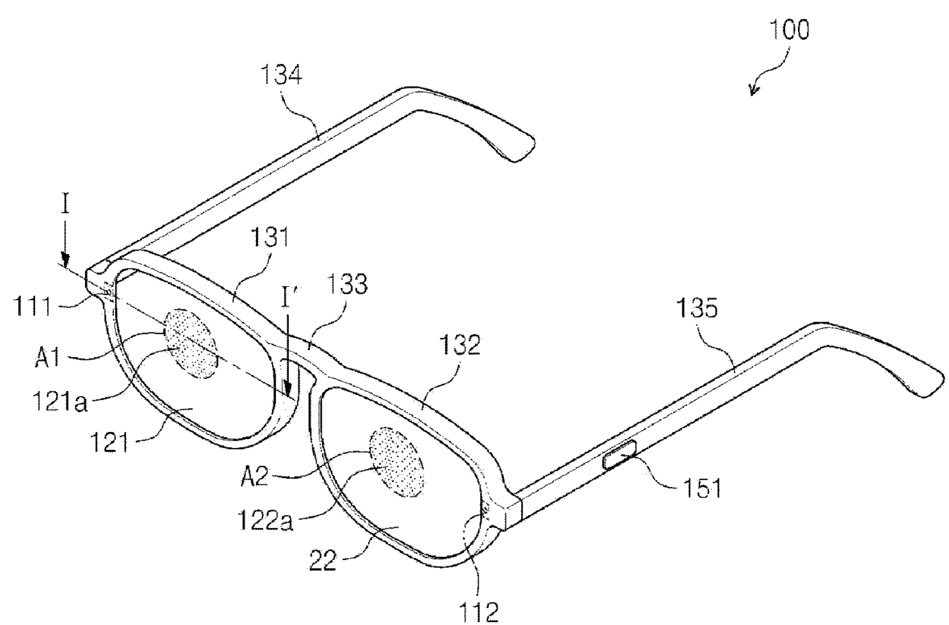
FIG. 2 is a perspective view of the pair of awareness glasses of FIG. 1, according to exemplary embodiments.

FIG. 1 is a block diagram of a pair of awareness glasses, according to exemplary embodiments. FIG. 2 is a perspective view of the pair of awareness glasses of FIG. 1.

Referring to FIG. 1, the pair of awareness glasses (or glasses) 100 includes a light source unit 110, a lens unit 120, a driving unit 140, and a switch unit 150.

The light source unit 110 includes a first light source 111 and a second light source 112. Each of the first and second light sources 111 and 112 may include a light emitting diode or any other suitable light generating device. Receiving a power, the first and second light sources 111 and 112 generate light to be supplied to the lens unit 120. The light generated from the first and second light sources 111 and 112 may include light with a peak wavelength between 444 nm and 484 nm, such as 454 nm and 474 nm, e.g., 462 nm and 468 nm.

The driving unit 140 supplies power to the first and second light sources 111 and 112. The driving unit 140 includes a battery 141 and first and second wiring units 142 and 143. The battery 141 may be or include at least one of a rechargeable battery and a coin battery or some other non-rechargeable power source. When configured as a rechargeable battery, the battery 141 may be configured to be charged and recharged. Although not shown in FIG. 1, a display unit (or any other suitable visual, audible, or tactile indicator) may be further included, which may generate an interrupt signal based on whether the battery 141 is at a low power or necessitates charging, as well as provides the interrupt signal to a user. The display unit may determine, in a low-power state, that a voltage of the battery 141 is lower than a constant (or threshold) voltage (e.g., 3.3 V) and may generate a battery low-power interrupt signal based on a result of the determination. If the battery 141 is a rechargeable battery, the display unit may generate a battery charge interrupt signal. The first wiring unit 142 supplies power from the battery 141 to the first light source 111, and the second wiring unit 143 supplies power from the battery 141 to the second light source 112.

The switch unit 150 includes a power switch 151 that switches (or otherwise controls the flow of) power in the pair of glasses 100. The power switch 151 may be manually turned on or off by a user. The switch unit 150 further includes a mode selection unit 152 that allows a user to select one of a first mode and a second mode, e.g., an awareness mode and a normal mode. The mode selection unit 152 controls an operation of the power switch 151 in response to a mode selection signal generated based on input from the user. For example, if the user selects the awareness mode, the mode selection unit 152 turns the power switch 151 on, which enables the driving unit 140 to supply power to the light source unit 110. If the user selects the normal mode, the mode selection unit 152 turns the power switch 151 off. This prevents the driving unit 140 from supplying power to the light source unit 110.

The lens unit 120 includes a first light guide lens 121 and a second light guide lens 122 corresponding to the eyes of a user of the pair of glasses 100. The first and second light guide lenses 121 and 122 are formed of any suitable material with a total reflection property. For example, the first and second light guide lenses 121 and 122 may be formed of a polymethyl methacrylate (PMMA) material. Again, however, any other suitable material may be utilized in association with exemplary embodiments described herein.

The first light guide lens 121 provides a left eye of the user with light from the first light source 111, and the second light guide lens 122 provides a right eye of the user with light from the second light source 112, or vice versa. Each of the first and second light guide lenses 121 and 122 may include a diffraction grating pattern that provides both eyes of the user with a determined wavelength component of the light. The diffraction grating pattern is described in more detail in with reference to FIGS. 3 and 4.

Referring to FIG. 2, the pair of awareness glasses 100 further includes a glasses frame (or frame). The frame includes a first rim 131 coupled to an edge of the first light guide lens 121 and a second rim 132 coupled to an edge of the second light guide lens 122. The shape of the first and second rims 131 and 132 may be formed in correspondence with the shapes of the first and second light guide lenses 121 and 122. The frame includes a bridge 133 connecting the first rim 131 and the second rim 132, a first temple 134 hinge-jointed (or otherwise coupled) to an end of the first rim 131, and a second temple 135 hinge-jointed (or otherwise coupled) to an end of the second rim 132. The driving unit 140 (not illustrated in FIG. 2) may be embedded in one of the first and second temples 134 and 135. It is also contemplated that the driving unit 140 may be disposed on or in any other suitable component of the frame.

The first light source 111 is disposed adjacent to a side of the first light guide lens 121 and is embedded in (or otherwise coupled to) the first rim 131. The second light source 112 is disposed adjacent to a side of the second light guide lens 122 and is embedded in (or otherwise coupled to) the second rim 132. Portions of the first and second rims 131 and 132 that are joined via the bridge 133 may be referred to as first ends of the first and second rims 131 and 132, and the other portions of the first and second rims 131 and 132 may be referred to as second ends of the first and second rims 131 and 132. The first and second light sources 111 and 112 may be disposed at the second ends of the first and second rims 131 and 132. It is contemplated, however, that the first and second light sources 111 and 121 may be disposed in or on any other suitable component of the pair of glasses 100.

The first and second temples 134 and 135 are respectively hinge-jointed to the first and second rims 131 and 132. In this manner, the first and second temples 134 and 135 may be folded or otherwise rotated about corresponding axes of rotation associated with the hinge joints of the first and second rims 131 and 132. If the battery 141 of the driving unit 140 is placed (or otherwise disposed) at a side of the second temple 135, the first wiring unit 142 may be arranged along the second temple 135, the second rim 132, the bridge 133, and the first rim 131 to be electrically connected to the first light source 111. The second wiring unit 143 may be arranged along the second temple 135 and the second rim 132 to be electrically connected to the second light source 112. It is contemplated, however, that the battery 141 may be disposed in association with any other suitable component of the pair of glasses 100, such that the first and second wiring units 142 and 143 may be configured in any suitable matter to enable electrical connection between the battery 141 and the first and second light sources 111 and 121.

In FIG. 2, the battery 141 is built in the second temple 135. Again, it is contemplated that any other suitable arrangement may be utilized in association with exemplary embodiments described herein. For example, the battery 141 may be built in the second rim 132, such that lengths of the first and second wiring units 142 and 143 are shortened. The first and second wiring units 142 and 143 may be disposed such that they are buried (or otherwise embedded) in the second temple 135 and the first and second rims 131 and 132.

As illustrated in FIG. 2, center portions (or any other suitable portions) of the first and second light guide lenses 121 and 122 may be defined as first and second grating areas A1 and A2, respectively. The first light guide lens 121 includes a first diffraction grating pattern 121*a* formed in the first grating area A1, and the second light guide lens 122 includes a second diffraction grating pattern 122*a* formed in the second grating area A2. If a user wears the awareness glasses 100, the first and second grating areas A1 and A2 may be defined by areas respectively corresponding to the eyes of the user. The first and second grating areas A1 and A2 may have a diameter of about 1 mm to 3 cm, such as 7 mm to 24 mm, e.g., 12 mm to 19 mm.

Figure 3:
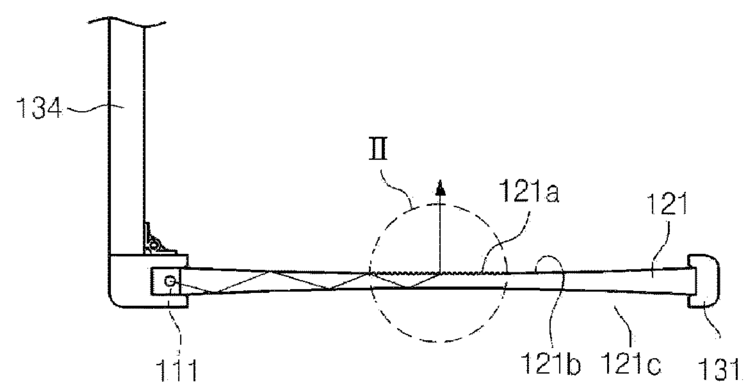
FIG. 3 is a cross-sectional view of the pair of awareness glass of FIG. 2 taken along sectional line I-I', according to exemplary embodiments.
Figure 4:
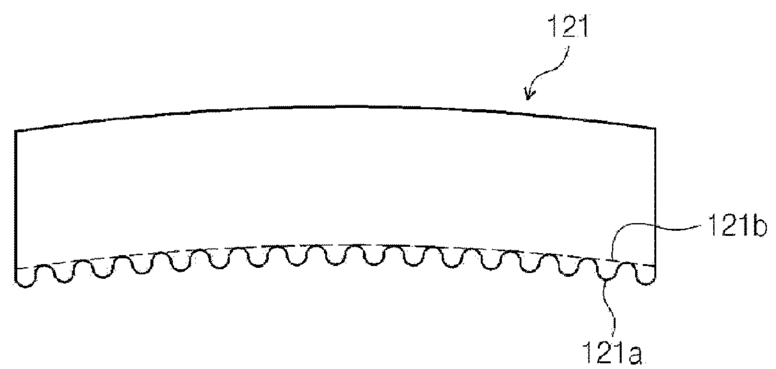
FIG. 4 is an enlarged view of portion II of the pair of awareness glasses of FIG. 3, according to exemplary embodiments.

FIG. 3 is a cross-sectional view of the pair of awareness glasses of FIG. 2 taken along sectional line I-I', according to exemplary embodiments. FIG. 4 is an enlarged view of portion II of the pair of awareness glasses of FIG. 3.

Referring to FIGS. 3 and 4, when a user wears awareness glasses 100, one surface (e.g., an inner surface) of a first light guide lens 121 facing a left eye of the user may be referred to as a light output surface 121*b*, and a surface facing the light output surface 121*b* may be referred to as an opposite surface (or an outer surface) 121*c*.

The first diffraction grating pattern 121*a* may have a shape protruding from the light output surface 121*b* of the first light guide lens 121 towards a left eye of the user. Although not shown, the second diffraction grating pattern 122*a* may have a shape protruding from a light output surface of the second light guide lens 122 towards a right eye side of the user. It is also contemplated that the first and second diffraction grating patterns 121*a* and 122*a* may be formed on the opposite surfaces (e.g., opposite surface 121*c*) of the first and second light guide lenses 121 and 122. To this end, any suitable combination of diffraction grating patterns may be formed on the light output surface 121*b* and the opposite surface 121*c* to form the first and second diffraction grating patterns 121*a* and 122*a* of the first and second light guide lenses 121 and 122.

A light, satisfying a total reflection condition of the first light guide lens 121, of a light output from the first light source 111 may be guided via the first light guide lens 121. The guided light may be incident on the first diffraction grating pattern 121*a*. When the light arrives at the first diffraction grating pattern 121*a*, it may penetrate the diffraction grating pattern 121*a* to be diffracted. A light output via the diffraction grating pattern 121*a* may be of a wavelength, which may be determined according to Equation (1). That is, Equation (1) may be a diffraction grating formula with respect to a diffraction angle θc and an incident angle θi with respect to a line perpendicular to the light output surface 121*b*.

$$d(\sin(\theta i)+\sin(\theta c))=m\lambda \quad \text{Eq. (1)}$$

In Equation (1), "m" indicates a diffraction degree, "λ" indicates a wavelength of output light, and "d" indicates a period of the diffraction grating pattern. Further, "θi" indicates an incident angle and "θc" indicates a diffraction angle.

If a critical angle of a total reflection condition of the first and second light guide lenses 121 and 122 is, for example, 41.8°, the diffraction angle θc may have an angle greater than at least 41.8°. It is noted that a front light output condition, e.g., where light with a wavelength of 464 nm is output to a left eye of a user to be perpendicular to the light output surface 121*b*, may include the incident angle θi of 0°, a diffraction angle θc of 41.8°, and a wavelength of 464 nm. If the front light output condition is substituted in Equation (1), a period d of the first diffraction grating pattern 121*a* may be about 692.5 nm. To this end, the diffraction angle θc may be between 41.8° and 90°. As such, if a desired wavelength of output light is 464 nm, periods d of the first and second diffraction grating patterns 121*a* and 122*a* may be set to be within a range of 464 nm<d<692.5 nm. If a desired wavelength of output light is changed or a range of the diffraction angle θc is different, a range of periods d of the first and second diffraction grating patterns 121*a* and 122*a* may be different than as previously described.

According to exemplary embodiments, first and second rims 131 and 132 may be formed of any suitable material, such as, for example, a metallic material or a material having a high reflectance. Light loss may be reduced by preventing light from the first and second light sources 111 and 112 from being leaked.

Figure 5:
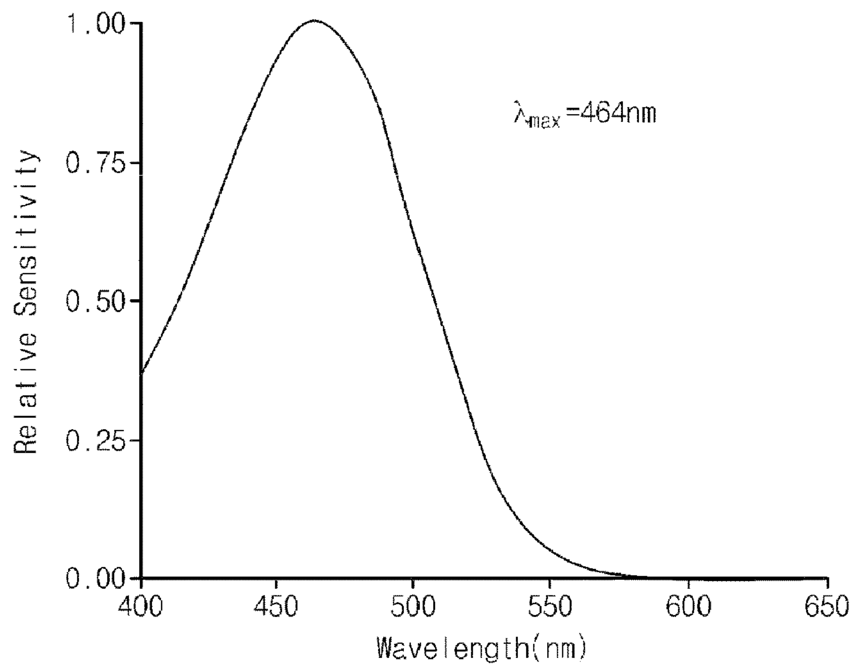
FIG. 5 is a graph showing an action spectrum of a melatonin inhibition ratio.
Figure 6:
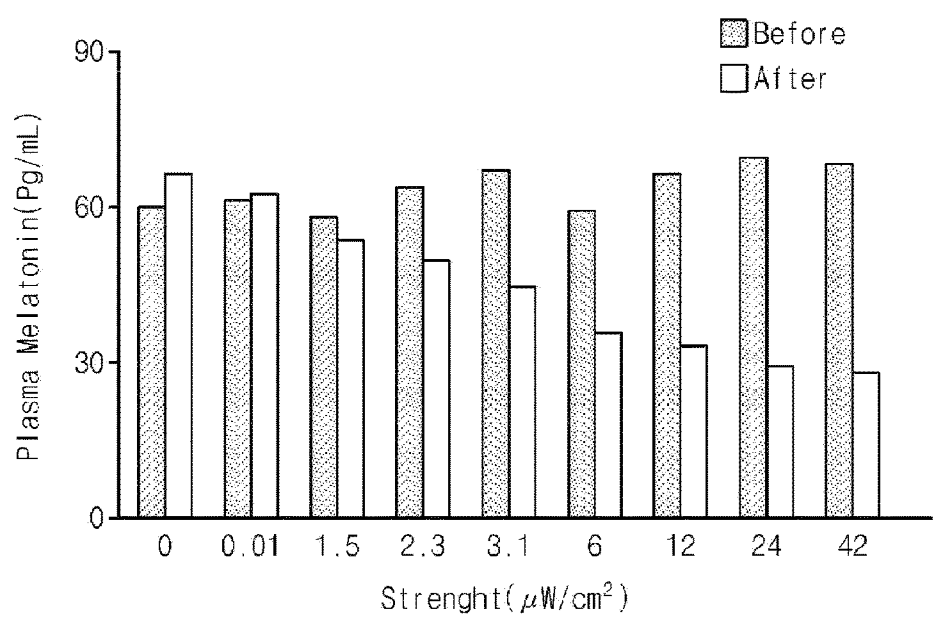
FIG. 6 is a graph showing a plasma melatonin value according to light intensity.

FIG. 5 is a graph showing an action spectrum of a melatonin inhibition ratio. FIG. 6 is a graph showing a plasma melatonin value according to light intensity. It is noted that, in FIG. 5, a melatonin inhibition ratio may indicate a log relative sensitivity.

Referring to FIG. 5, melatonin may be a hormone viewed as a criterion of physiological rhythm. That is, melatonin is a sleep hormone affecting awareness of the human body. When a level of melatonin is relatively high, a person may feel generally sleepy. When a level of melatonin is relatively low, an awareness effect may occur or otherwise be felt.

If light with a short wavelength is provided to the eyes of the human body, generation of melatonin of a recipient supplied with the light may be sharply decreased. For instance, a log relative sensitivity indicating a melatonin inhibition ratio may be at a maximum when a wavelength of the light is about 464 nm. The ratio may decrease as a wavelength of the light increases from 464 nm and may become zero as a wavelength of the light reaches (or otherwise approaches) 560 nm. In this manner, efficiency of melatonin inhibition may be improved by providing light with a peak wavelength of at least 444 nm to 484 nm to the eyes of the human body so that a person may feel generally aware and cognizant of their surroundings.

FIG. 6 shows a plasma melatonin inhibition degree (Pg/mL) before and after the eyes of a human body are exposed to light with a wavelength of 460 nm, according to light intensity (μW/cm$^2$). Referring to FIG. 6, when light intensity is greater than about 3.1, a plasma melatonin inhibition degree sharply increases, but when the light intensity is less than about 2.3, the plasma melatonin inhibition degree is shown to be relatively lower.

It is noted that the plasma melatonin inhibition degree may change with respect to light intensity and a location with which a peak wavelength of light belongs. For example, if the peak wavelength is longer or shorter than a wavelength of 464 nm having a maximum melatonin inhibition effect, the light intensity may accomplish a desired melatonin inhibition effect when the wavelength of the light becomes greater than 464 nm.

According to exemplary embodiments, light intensity may be provided according to whether the peak wavelength of the light has a value between 444 nm and 484 nm. If light output from the first and second light guide lenses 121 and 122 via the first and second diffraction grating patterns 121*a* and 122*a* is between 444 nm and 484 nm, then the output light may be sufficiently provided to the eyes of a user. As such, an effect of inhibiting the melatonin hormone generated in the human body of the user may be achieved. In this manner, if an individual wears the awareness glasses 100 during, for instance, a driving activity, danger due to drowsy driving may be reduced by an awareness effect provided via the glasses 100. Also, when the individual wears the awareness glasses 100 during working and learning activities, efficiency of the individuals work and study may be improved as a result of the awareness effect.

Figure 7A:
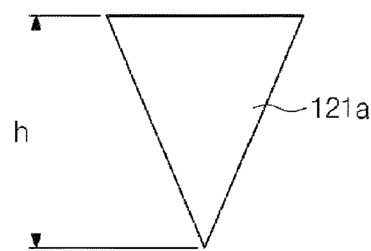
FIG. 7A illustrates a shape of a first diffraction grating pattern of FIG. 4, according to exemplary embodiments.
Figure 7B:
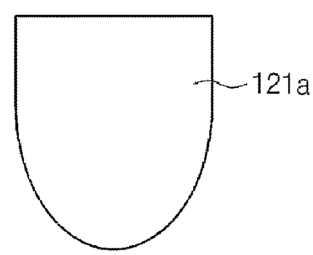
FIG. 7B illustrates a shape of a first diffraction grating pattern of FIG. 4, according to exemplary embodiments.
Figure 7C:
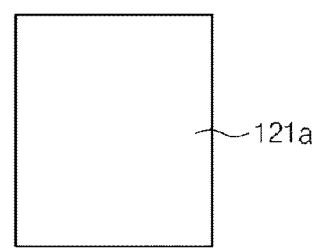
FIG. 7C illustrates a shape of a first diffraction grating pattern of FIG. 4, according to exemplary embodiments.

FIGS. 7A, 7B, and 7C each illustrate different shapes of first diffraction grating patterns of FIG. 4, according to exemplary embodiments. It is noted that the configuration of the second diffraction grating patterns 122*a* may be substantially similar to the configuration of the first diffraction grating patterns 121*a*. As such, to avoid obscuring exemplary embodiments described herein, duplicative descriptions are omitted.

Referring to FIGS. 7A to 7C, when seen in cross-section, a first diffraction grating pattern 121*a* may have a triangular pillar shape, a cylindrical pillar shape, a quadrilateral (e.g., square) pillar shape, and the like. The first diffraction grating pattern 121*a* may be configured such that its pitch, e.g., spacing between pillar shapes, has a rounded shape; however, it is contemplated that any other suitable shape may be utilized in association with exemplary embodiments described herein. To this end, it is noted that the shape of the first and second diffraction grating patterns 121*a* and 122*a* may be any suitable shape and may vary, and, thereby, not fixed to any particular shape. In exemplary embodiments, external quality (e.g., roughness of lenses) of the awareness glasses 100 may be improved if the heights h of the first and second diffraction grating patterns 121*a* and 122*a* are less than 10 μm. It is contemplated, however, that any suitable height h may be utilized in association with exemplary embodiments described herein.

Figure 8:
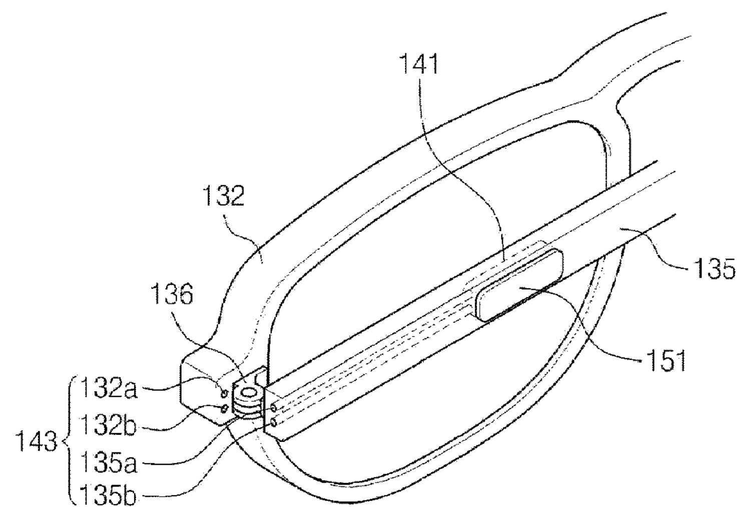
FIGS. 8 and 9 are partial perspective views of a pair of awareness glasses in two different states of a switching operation, according to exemplary embodiments.
Figure 9:
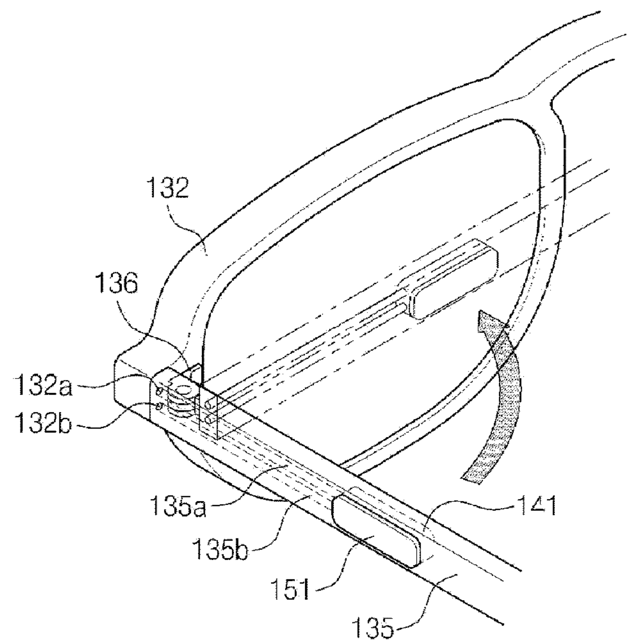

FIGS. 8 and 9 are partial perspective views of a pair of awareness glasses in two different states of a switching operation, according to exemplary embodiments.

Referring to FIGS. 8 and 9, a battery 141 and a power switch 151 are disposed at a second temple 135. A second wiring unit 143 includes a first driving voltage wiring 135*a*, a first ground wiring 135*b*, a second driving voltage wiring 132*a*, and a second ground wiring 132*b*. The first driving voltage wiring 135*a* and the first ground wiring 135*b* are buried (or otherwise embedded) in the second temple 135. The second driving voltage wiring 132*a* and the second ground wiring 132*b* are buried in a second rim 132. It is also contemplated that the one or more of the first driving voltage wiring 135*a*, the first ground wiring 135*b*, the second driving voltage wiring 132*a*, and the second ground wiring 132*b* may be disposed on the second temple 135 and/or the second rim 132.

According to exemplary embodiments, the second temple 135 and the second rim 132 may be hinge-jointed via a hinge 136. As such, the awareness glasses 100 may be folded and unfolded, and, thereby, configured in at least two operational states. As an example, an on/off operation of the awareness glasses 100 may be controlled by a folding and unfolding operation of the awareness glasses 100. That is, the first driving voltage wiring 135*a* and the first ground wiring 135*b* may be electrically connected to or disconnected from the second driving voltage wiring 132*a* and the second ground wiring 132*b* based on the folded and unfolded state of the awareness glasses 100. To this end, when the awareness glasses 100 are folded (e.g., in FIG. 8), the first driving voltage wiring 135*a* and the first ground wiring 135*b* may be electrically disconnected from the second driving voltage wiring 132*a* and the second ground wiring 132*b*. As such, the awareness glasses 100 may be turned off in the folded state of the awareness glasses 100. When the awareness glasses 100 are unfolded (e.g., in FIG. 9), the first driving voltage wiring 135*a* and the first ground wiring 135*b* may be electrically connected to the second driving voltage wiring 132*a* and the second ground wiring 132*b*. As such, the awareness glasses 100 may be turned on in the unfolded state of the awareness glasses 100. If a user does not turn the power switch 151 on in the unfolded state of the awareness glasses 100, the awareness glasses 100 may maintain in a turned-off state. When the power switch 151 is turned on, a state of the awareness glasses 100 may be switched to a turned-on state.

Figure 10:
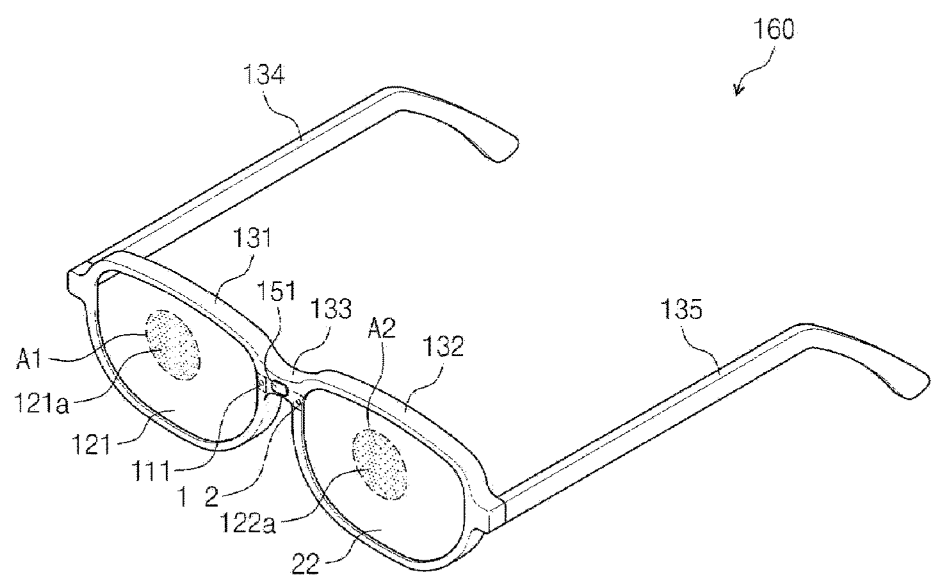
FIG. 10 is a perspective view of a pair of awareness glasses, according to exemplary embodiments.

FIG. 10 is a perspective view of a pair of awareness glasses, according to exemplary embodiments. The configuration of the pair of awareness glasses 160 illustrated in FIG. 10 is substantially similar to the configuration of the pair of awareness glasses 100 shown in FIG. 2. As such, to avoid obscuring exemplary embodiments described herein, duplicative descriptions are avoided and differences are described below.

Referring to FIG. 10, awareness glasses 160 include first and second light sources 111 and 112 disposed at (or near) ends of bridge 133. The first light source 111 supplies light to a first light guide lens 121 and the second light source 112 supplies light to a second light guide lens 122. A battery 141 and a power switch 151 are disposed between the first light source 111 and the second light source 112, and, thereby, are built in the bridge 133. If the battery 141, the power switch 151, and the first and second light sources 111 and 112 are embedded in the bridge 133, lengths of first and second wiring units 142 and 143 (not shown) may be shortened. As such, it is possible to simplify a fabricating process of the awareness glasses 160.

Although not shown, if a light source used in light source unit 110 comprises a diode (or a double-sided diode) having two output surfaces for outputting light in different directions, the awareness glasses 160 may provide light to the first and second light guide lenses 121 and 122 using only one double-sided light source instead of the first and second light sources 111 and 112. The double-sided light source may be placed at (or near) a center of the bridge 133. When turned on, the double-sided light source may power (or otherwise provide light to) the first and second light guide lenses 121 and 122 at the same time.

Figure 11:
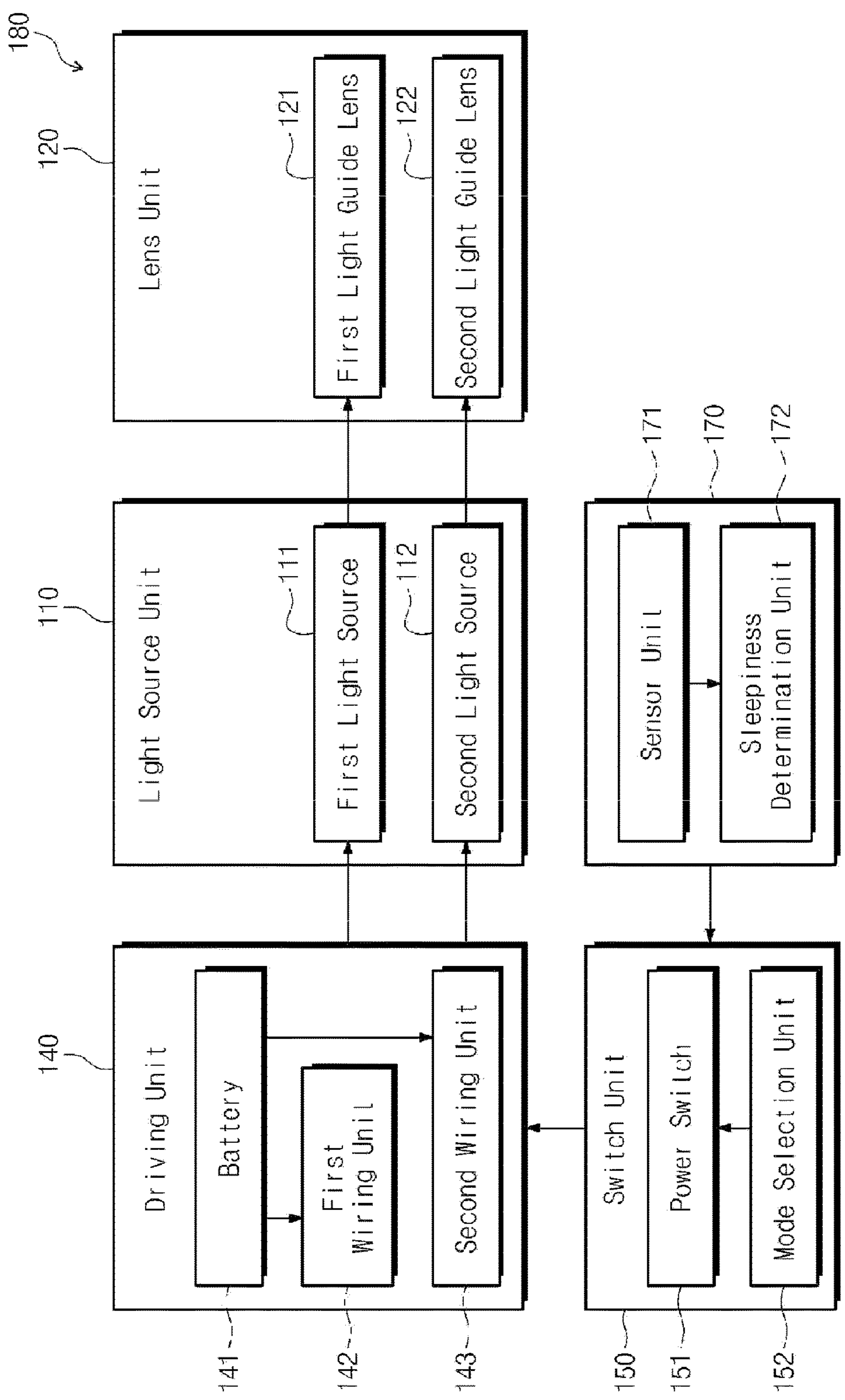
FIG. 11 is a block diagram of a pair of awareness glasses, according to exemplary embodiments.
Figure 12:
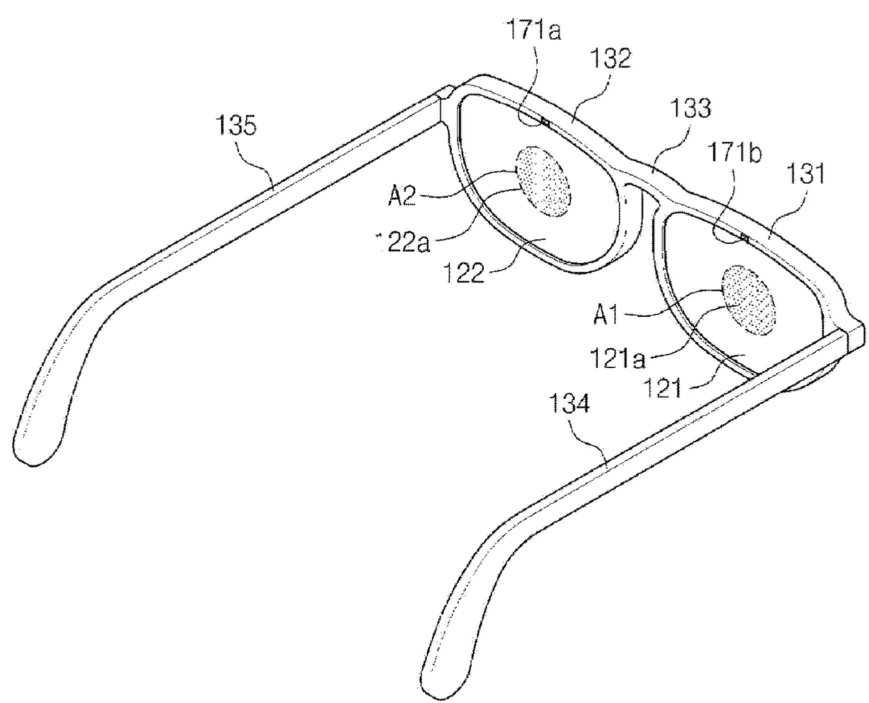
FIG. 12 is a perspective view of the pair of awareness glasses of FIG. 11, according to exemplary embodiments.

FIG. 11 is a block diagram of a pair of awareness glasses, according to exemplary embodiments. FIG. 12 is a perspective view of the pair of awareness glasses of FIG. 11. In FIGS. 11 and 12, the pair of awareness glasses 180 is configured substantially similar to the pair of awareness glasses 100 of FIGS. 1 and 2. As such, to avoid obscuring exemplary embodiments described herein, duplicative descriptions are avoided and differences are described below.

Referring to FIGS. 11 and 12, the pair of awareness glasses 180 detects sleepiness of a user via detection unit 170, as well as includes a driving unit 140 to drive a light source unit 110 according to the detection result.

Detection unit 170 includes a sensor unit 171 to detect sleepiness of a user and a sleepiness determination unit 172 to determine whether the user is drowsy, based on the detected data of the sensor unit 171. The sensor unit 171 may include one or more sensors to measure the number of blinks, a time when the user blinks, eye droopiness, blink duration, and/or the like. It is contemplated, however, that a type of the sensor to detect sleepiness may be of any suitable form. For example, a variety of sensors may be used to detect sleepiness of the user, such as one or more optical sensors, motion sensors, vibration sensors, and/or the like. It is also contemplated that the sensors may include one or more camera-based sensors and/or other like devices to record data associated with the eyes of a user of awareness glasses 180.

It is noted that the sensor unit 171 includes first and second sensors 171*a* and 171*b* respectively installed at first and second rims 131 and 132, as seen in FIG. 12. The first and second sensors 171*a* and 171*b* sense a left eye and a right eye of the user, respectively. The first and second sensors 171*a* and 171*b* may be a camera sensor. It is contemplated, however, that the inventive concept is not limited thereto. Also, the sensor unit 171 may be disposed at (or near) the bridge 133 to sense left and right eyes of the user at the same time or to sense any one of the left and right eyes of the user.

The sleepiness determination unit 172 measures a sleepiness level of the user based on the detected data of the sensor unit 171. If the sleepiness level of the user is higher than a reference sleepiness level, the switch unit 150 may be turned on, such that the driving unit 140 powers a light source unit 110. In this manner, the awareness glasses 180 may enter an awareness mode to arouse (or otherwise stimulate) a user of the awareness glasses 180. If the sleepiness level of the user is lower than the reference sleepiness level, the switch unit 150 may be turned off, and, as such, the awareness glasses 180 may enter a normal mode instead of the awareness mode. As such, sensor unit 171 may enable the awareness glasses 180 to be automatically switched between operational modes without manually selecting the awareness mode and the normal mode by a user. Accordingly, as a user wears the awareness glasses 180 during, for example, a driving activity, a danger due to drowsy driving may be reduced by an awareness effect when the awareness mode is activated. Also, when a user wears the awareness glasses 180 during, for instance, a working and learning activity, an efficiency level of work and study may be improved by the awareness effect.

In exemplary embodiments, the determination unit 170, and/or one or more components thereof, may be implemented via one or more general purpose and/or special purpose components, such as one or more discrete circuits, digital signal processing chips, integrated circuits, application specific integrated circuits, microprocessors, processors, programmable arrays, field programmable arrays, instruction set processors, and/or the like.

According to exemplary embodiments, the features, functions, processes, etc., described herein for sleepiness determination may be implemented via software, hardware (e.g., general processor, digital signal processing (DSP) chip, an application specific integrated circuit (ASIC), field programmable gate arrays (FPGAs), etc.), firmware, or a combination thereof. In this manner, the determination unit 170, and/or one or more components thereof, may include or otherwise be associated with one or more memories (not shown) including code (e.g., instructions) configured to cause the determination unit 170, and/or one or more components thereof, to perform one or more of the features, functions, processes, etc., described herein.

The memories may be any medium that participates in providing code to the one or more software, hardware, and/or firmware components for execution. Such memories may be implemented in any suitable form, including, but not limited to, non-volatile media, volatile media, and transmission media. Non-volatile media include, for example, optical or magnetic disks. Volatile media include dynamic memory. Transmission media include coaxial cables, copper wire and fiber optics. Transmission media can also take the form of acoustic, optical, or electromagnetic waves. Common forms of computer-readable media include, for example, a floppy disk, a flexible disk, hard disk, magnetic tape, any other magnetic medium, a compact disk-read only memory (CD-ROM), a rewriteable compact disk (CDRW), a digital video disk (DVD), a rewriteable DVD (DVD-RW), any other optical medium, punch cards, paper tape, optical mark sheets, any other physical medium with patterns of holes or other optically recognizable indicia, a random-access memory (RAM), a programmable read only memory (PROM), and erasable programmable read only memory (EPROM), a FLASH-EPROM, any other memory chip or cartridge, a carrier wave, or any other medium from which information may be read by, for example, a controller/processor.

Figure 13:
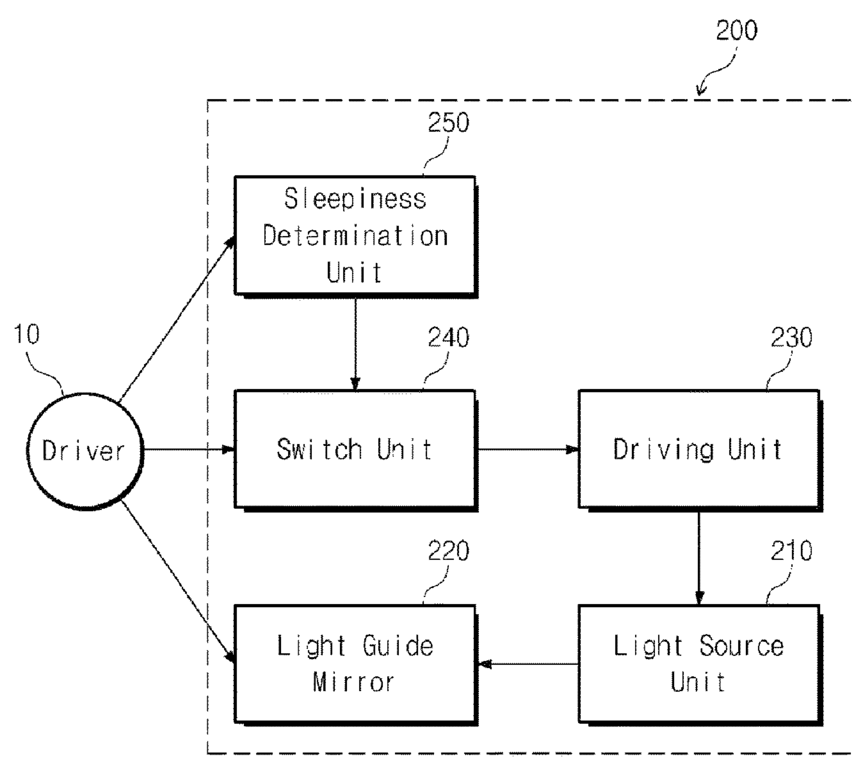
FIG. 13 is a block diagram of a car mirror unit with an awareness function, according to exemplary embodiments.
Figure 14:
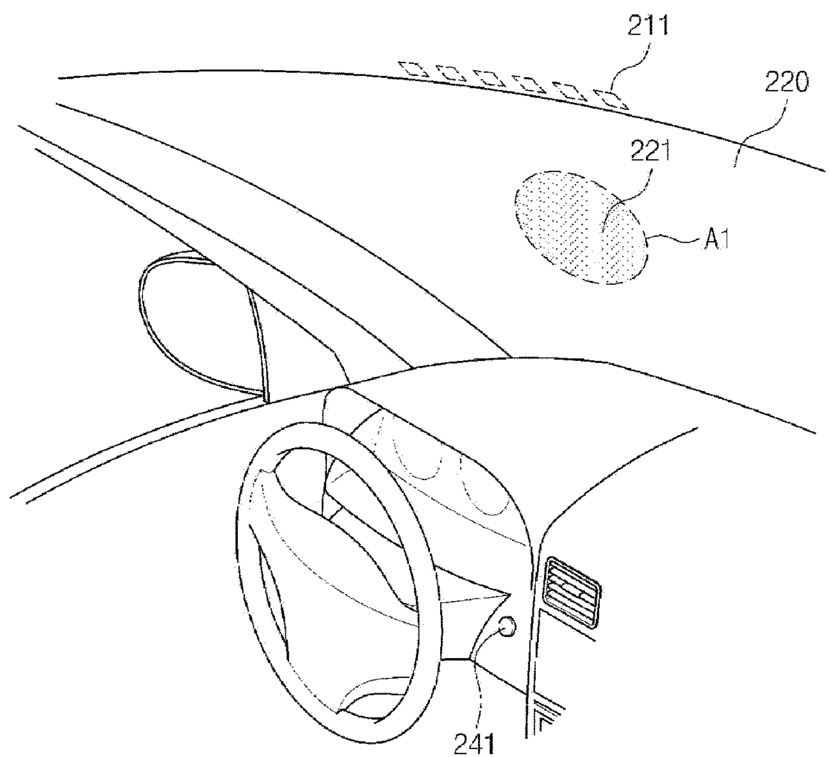
FIG. 14 is a car including the car mirror unit of FIG. 13, according to exemplary embodiments.

FIG. 13 is a block diagram of a car mirror unit with an awareness function, according to exemplary embodiments. FIG. 14 is a car including the car mirror unit of FIG. 13, according to exemplary embodiments.

Referring to FIG. 13, a car mirror unit 200 has an awareness function and includes a light source unit 210, a light guide mirror 220, a driving unit 230, a switch unit 240, and a sleepiness determination unit 250.

According to exemplary embodiments, the light source unit 210 includes one or more light sources 211, each of which is formed of a light emitting diode or any other suitable light source. When the light source unit 210 is powered, the light source unit 210 generates light to be supplied to a light guide mirror 220. The light may include light with a peak wavelength between 444 nm and 484 nm, such as 454 nm and 474 nm, e.g., 462 nm and 468 nm.

The driving unit 230 supplies a driving voltage to the light source unit 210. The driving unit 230 includes a voltage conversion unit 211 and a power wiring (not shown) to transfer power between the voltage conversion unit 211 and the light source unit 210 and/or one or more other components of the driving unit 230. The voltage conversion unit 211 converts a power supplied from a power supply unit (not shown) of the car into the driving voltage for driving the light source unit 210. The power wiring supplies the driving voltage to the light source unit 210.

The switch unit 240 includes a power switch 241 that switches a supplied power to the driving unit 230. The power switch 241 disposed adjacent to, for example, a driver's seat of the car. The power switch 241 may be manually turned on or off by a driver 10. The switch unit 240 may further include a mode selection unit (not shown) to allow the driver 10 to select one of an awareness mode and a normal mode. When the driver 10 selects the awareness mode, the mode selection unit may turn the power switch 241 on, such that the driving voltage is supplied to the light source unit 210. When the driver 10 selects the normal mode, the mode selection unit may turn the power switch 241 off, such that the driving voltage is not supplied to the light source unit 210.

The sleepiness determination unit 250 detects sleepiness of the driver 10 and may be configured to turn the switch unit 240 on or off based on the detection result. The sleepiness determination unit 250 may be configured similarly as the determination unit 170 of FIG. 11.

Although not shown, the car mirror unit 220 may include one or more sensors to detect data for determining sleepiness of the driver 10. Whether the driver 10 is drowsy may be determined according to the data detected by the sensor. The sensor may be a sensor to measure the number of blinks, a time when the user blinks, eye droopiness, blink duration, and/or the like. It is contemplated, however, that a type of the sensor to detect sleepiness may be of any suitable form. For example, a variety of sensors may be used to detect sleepiness of the user, such as one or more optical sensors, motion sensors, vibration sensors, and/or the like. It is also contemplated that the sensors may include one or more camera-based sensors and/or other like devices to record data associated with the eyes of a user of the car mirror unit 200.

According to exemplary embodiments, the sleepiness determination unit 250 measures a sleepiness level of the driver based on the detected data. If the sleepiness level of the driver is higher than a reference sleepiness level, the switch unit 240 may be turned on, such that the driving voltage is supplied from the driving unit 230 to the light source unit 210. If the sleepiness level of the driver is lower than the reference sleepiness level, the switch unit 240 may be turned off, such that the car mirror unit 200 operates in a normal mode.

As illustrated in FIG. 14, the light guide mirror 220 includes a grating area A1, which may be defined at a driver side to have a size corresponding to the face of the driver 10. The light guide mirror 220 includes a diffraction grating pattern 221 formed in the grating area A1. The diffraction grating pattern 221 may be similar to the first diffraction grating pattern 121*a* of FIGS. 2-4 and may have various shapes, such as described with reference to FIGS. 7A to 7C. As such, a duplicative description of the diffraction grating pattern 221 is omitted.

In exemplary embodiments, if a peak wavelength of light output from the light guide mirror 220 according to a period of the diffraction grating pattern 221 exists between 444 nm and 484 nm, output light may be supplied to the eyes of the driver 10. In this manner, an effect of inhibiting melatonin hormone generated in the human body of the driver 10 may be provided. As such, it may be possible to prevent (or otherwise reduce) sleepiness driving and accidents due to sleepiness driving.

Figure 15:
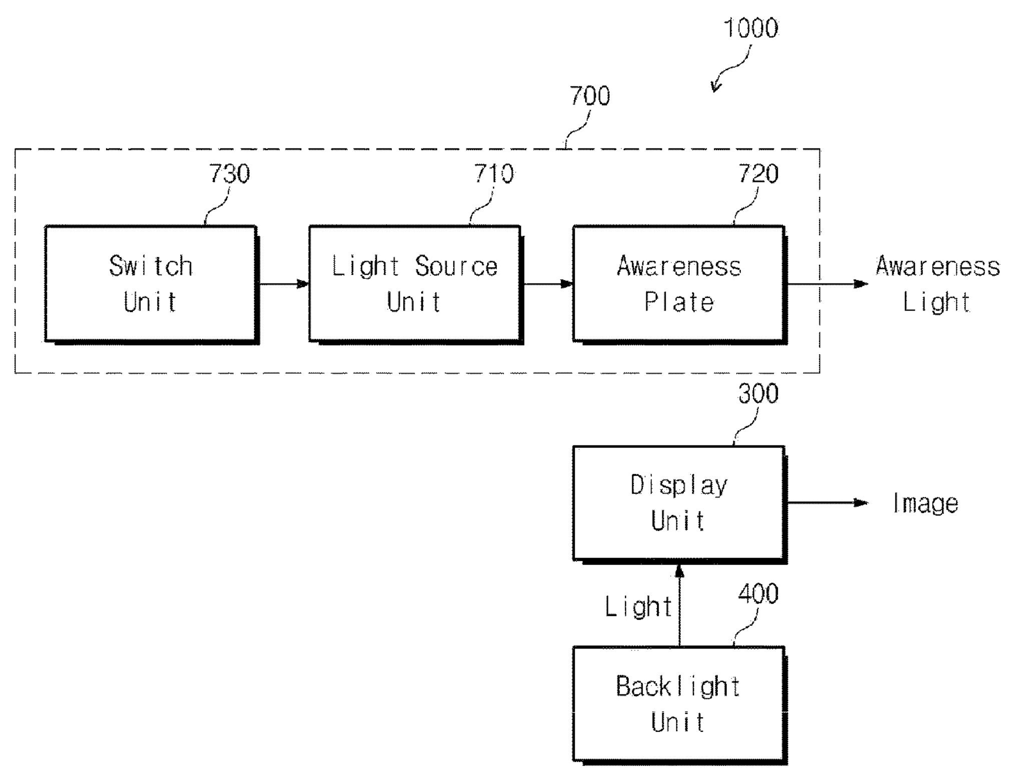
FIG. 15 is a block diagram of a display apparatus with an awareness function, according to exemplary embodiments.
Figure 16:
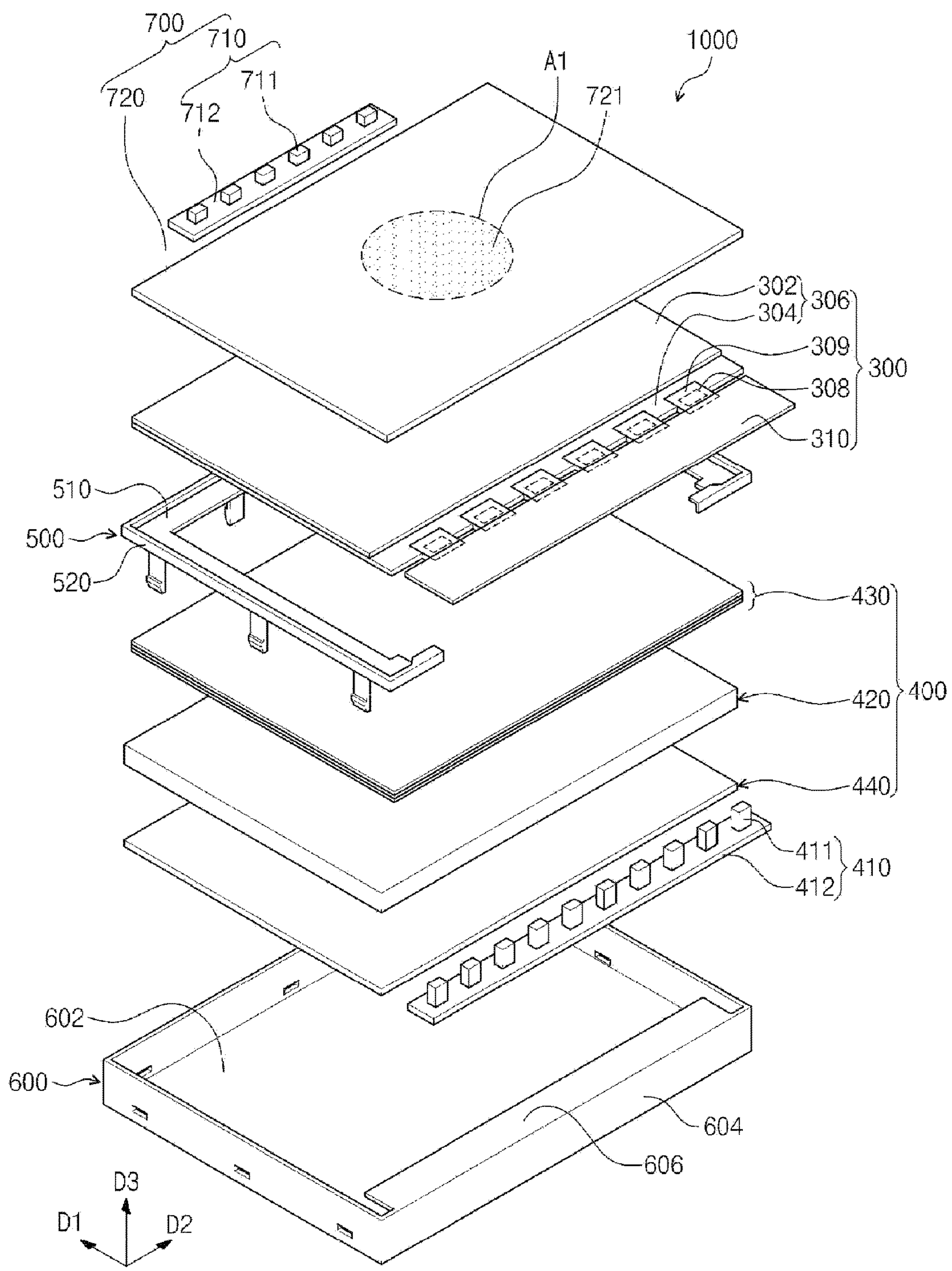
FIG. 16 is an exploded perspective view of the display apparatus of FIG. 15, according to exemplary embodiments.

FIG. 15 is a block diagram of a display apparatus with an awareness function, according to exemplary embodiments. FIG. 16 is an exploded perspective view of the display apparatus of FIG. 15.

Referring to FIGS. 15 and 16, a display apparatus 1000 with an awareness function includes a display unit 300 which receives light to display an image, a backlight unit 400 that supplies the light to the display unit 300, and an awareness optical unit 700 disposed between the display unit 300 and a user to supply light with a specific wavelength to the user to awaken the user.

As illustrated in FIG. 16, the display device 1000 further includes a mold frame 500 and a bottom chassis 600. When viewed in a plan view, the display device 1000 may have a rectangular structure, however, any other suitable configuration may be utilized in association with exemplary embodiments described herein. A short-edge direction of the display device 1000 is defined as a first direction D1, and a long-edge direction of the display device 1000 is defined as a second direction D2 perpendicular to the first direction D1. Also, the bottom chassis 600, the backlight unit 400, the mold frame 500, and the display unit 300 of the display device 1000 may be sequentially stacked in a third direction D3 perpendicular to the first and second directions D1 and D2.

The display unit 300 includes a display panel 306 to display an image, a driving chip 308 to provide a driving signal to the display panel 306, and a printed circuit board 310 electrically connected to the display panel 306. The display panel 306 includes a first substrate 302, a second substrate 304 opposite the first substrate 302, and a liquid crystal layer (not shown) disposed between the first substrate 302 and the second substrate 304. It is noted that although FIG. 16 is an exemplary liquid crystal display, it is contemplated that any other suitable display may be utilized in association with exemplary embodiments described herein, such as, for example, organic light emitting diode (OLED) displays, plasma displays (PDs), field emission displays (FEDs), electrophoretic displays (EPDs), electrowetting displays (EWDs), and the like.

The first substrate 302 may include a plurality of pixels (not shown) arranged in a matrix form, and each pixel may have a gate line (not shown) extending along the first direction D1, a data line (not shown) extending along the second direction D2 and disposed to cross the gate line (but isolated therefrom), and a pixel electrode (not shown). Also, each pixel may have a thin film transistor (not shown) connected to the gate line, the data line, and the pixel electrode.

In exemplary embodiments, RGB pixels (not shown), or color pixels, and a common electrode (not shown) facing the pixel electrodes may be formed on the second substrate 304. Alternatively, the color pixels and the common electrode may be formed on the first substrate 302. The liquid crystal layer may be arranged according to the strength of an electric field formed between the pixel electrode and the common electrode, and may facilitate the display of a desired gray scale by adjusting transmittance of light from the backlight unit 400.

As seen in FIG. 16, the driving chip 308 may be provided on at least one side of the first substrate 302 to apply a data signal to the data line. The driving chip 308 responds to an external signal to generate a data signal to be applied to the data line of the display panel 306. The external signal may be provided from the printed circuit board 310 and may include an image signal, various control signals, a driving voltage, etc.

The first substrate 302 may include a gate driving circuit that is provided on a side different from the at least one side that the driving chip 308 is disposed on. The gate driving circuit may apply a gate signal to the gate line. The gate driving circuit may be formed on the different side through a thin film process for forming the display panel 306. As such, the gate driving circuit may be embedded in the display panel 306. It is also contemplated that the driving chip 308 may be formed of two or more chips divided into a data driving chip and a gate driving chip. These chips may be mounted on the first substrate 302 through a chip on glass process or any other suitable manufacturing technique.

The printed circuit board 310 is electrically connected to the display panel 306 via a plurality of tape carrier packages 309. The driving chip 308 is mounted on the tape carrier packages 309. The tape carrier packages 309 may be curved to cover a side of the bottom chassis 600. The printed circuit board 310 connected to the tape carrier packages 309 is disposed on a bottom of the bottom chassis 600. In this manner, the display device 1000 may further comprise a shield case (not shown), which may be disposed at a bottom of the bottom chassis 600 to protect the printed circuit board 310. Although not shown, the printed circuit board 310 may be disposed on a sidewall of the bottom chassis 600.

The backlight unit 400 includes a backlight 410 to generate light and a light guide plate 420 to guide the light provided from the backlight 410 to the display unit 300. In exemplary embodiments, the backlight unit 400 may be an edge type backlight unit. That is, the backlight 410 of the backlight unit 400 may provide light from a bottom of the display panel 306 to at least one sidewall of the light guide plate 420, and the light guide plate 420 may guide the light to the display unit 300.

According to exemplary embodiments, the backlight 410 includes a plurality of light emitting diodes 411 that are sequentially arranged along one side of the light guide plate 420. The backlight 410 further includes a support film 412 on which the plurality of light emitting diodes 411 may be mounted. The light emitting diodes 411 are spaced apart from one another in the second direction D2. The backlight unit 400 further includes a plurality of optical sheets 430 provided between the light guide plate 420 and the display unit 300, and a reflection plate 440 disposed under the light guide plate 420.

The plurality of optical sheets 430 may be formed of a diffusion sheet for diffusing light and at least one condensing sheet for concentrating the light. The optical sheets 430 may improve luminance and a viewing angle of light output from a light output surface of the display apparatus 1000. Although not shown, the plurality of optical sheets 430 may further include a protection sheet that is provided on the uppermost layer of the optical sheets 430. The reflection plate 440 may be provided under the light guide plate 420. The reflection plate 440 may reflect light leaked from the light guide plate 420 so as to be provided to the light guide plate 420.

The bottom chassis 600 includes a bottom portion 602 on which the backlight unit 400 is supported, a sidewall 604 extending from the bottom portion 602 in a vertical direction (i.e., the third direction D3), and a cover portion 606 extending from the sidewall 604 in a direction parallel to the bottom portion 602 and configured to cover the backlight 410.

The mold frame 500 is disposed between the display unit 300 and the backlight unit 400 to support the display panel 306. The mold frame 500 includes a support portion 510 to support the display panel 306 and a sidewall 520 extending from the support portion 510 in the third direction D3. The mold frame 500 is configured to expose the cover portion 606 of the bottom chassis 600 by partially removing the support portion 510 and the sidewall 520 adjacent to the backlight 410. The display panel 306 is supported on the cover portion 606 at a region adjacent to the backlight 410. A fixing tape (not shown) may be attached (or otherwise coupled) to an edge of the display panel 306 to fix the display panel 306 to the mold frame 500. It is also contemplated that, instead of the fixing tape, the display device 1000 may further include a top chassis (not shown) that is joined to and disposed opposite of the bottom chassis 600. The top chassis may cover an edge of the display panel 306.

The awareness optical unit 700 is disposed on the display unit 300. The awareness optical unit 700 includes a light source unit 710 and an awareness plate 720. The light source unit 710 includes a plurality of light sources 711 and a circuit film 712. The plurality of light sources 711 is mounted on the circuit film 712, and a driving circuit unit (not shown) may be further included to supply a driving voltage to the light sources 711.

The awareness plate 720 may have a plate shape formed to have a size corresponding to the size of the display unit 300. The awareness plate 720 includes a diffraction grating pattern 721 that is formed in a grating area A1 defined at (or near) a center of the awareness plate 720. The diffraction grating pattern 721 may be formed on either an upper surface or a lower surface of the awareness plate 720. A shape of the diffraction grating pattern 721 may be similar to that of the first diffraction grating pattern 121*a* shown in FIGS. 2-4, and the diffraction grating pattern 721 may have various shapes as described with reference to FIGS. 7A to 7C. As such, a duplicative description of the diffraction grating pattern 721 is omitted.

In exemplary embodiments, if a peak wavelength of an awareness light output from the awareness plate 720 according to a period of the diffraction grating pattern 721 is between 444 nm and 484 nm, the awareness light may be supplied to the eyes of a user. In this manner, an effect of inhibiting melatonin hormone generated in the human body of the user may be provided.

The awareness optical unit 700 may also include a switch unit 730. The switch unit 730 may include a power switch (not shown), the operation of which switches on and off the light source unit 710. The power switch may be provided at a computer monitor, a portable phone, a television, etc., and may be manually turned on or off by a user. In this manner, when using a computer, a portable phone, watching a television, etc., a user thereof may feel an awareness effect using a simple switch operation to get rid of sleepiness. In this manner, an efficiency level of work and study may be improved by the awareness effect.

Although certain exemplary embodiments and implementations have been described herein, other embodiments and modifications will be apparent from this description. Accordingly, the inventive concept is not limited to such embodiments, but rather to the broader scope of the presented claims and various obvious modifications and equivalent arrangements.

What is claimed is:

1. A vehicular windshield apparatus, comprising:

a plurality of light emitting diodes configured to generate light in response to a driving voltage, the plurality of light emitting diodes being adjacent to each other and disposed in front of a driver;

a power source configured to supply the driving voltage to the plurality of light emitting diodes;

a windshield forming a light guide, the light guide being configured to:

receive the light from the plurality of light emitting diodes through a peripheral surface of the windshield; and guide, via total internal reflection, the light from the peripheral surface to a predetermined portion of the windshield disposed in front of the driver; and a diffraction grating pattern formed on a surface of the predetermined portion of the windshield, the diffraction grating pattern being configured to receive, diffract, and redirect the light from the plurality of light emitting diodes to eyes of the driver, wherein light output from the diffraction grating pattern has a peak wavelength between 444 nm and 484 nm, wherein the windshield comprises:

a light output surface facing the driver;

an opposite surface opposing the light output surface; and the peripheral surface extending between the light output surface and the opposite surface, and wherein the plurality of light emitting diodes are spaced apart from the windshield along the peripheral surface and disposed between the light output surface and the opposite surface.

2. The vehicular windshield apparatus of claim 1, wherein a period of the diffraction grating pattern is within a range between 464 nm and 692.5 nm.

3. The vehicular windshield apparatus of claim 1, wherein the diffraction grating pattern comprises one of a triangular pillar shape, a cylindrical pillar shape, and a quadrilateral pillar shape.

4. The vehicular windshield apparatus of claim 1, further comprising:

a power switch coupled between the power source and the plurality of light emitting diodes, wherein, in response to a manual input from the driver, the power switch is configured to electrically couple the power source and the plurality of light emitting diodes to transfer the driving voltage to the plurality of light emitting diodes.

5. The vehicular windshield apparatus of claim 1, further comprising:

at least one sensor;

at least one processor; and at least one memory comprising reference information, the at least one memory further comprising one or more sequences of one or more instructions that, in response to being executed by the at least one processor, cause the at least one processor at least to:

receive output from the at least one sensor; and compare the output with the reference information, wherein, in response to the output being greater than the reference information, the at least one processor is further configured to:

cause, at least in part, the driving voltage to be supplied to the plurality of light emitting diodes; and modulate the light output according to the output from the at least one sensor to inhibit melatonin production in the driver.

6. The vehicular windshield apparatus of claim 1, wherein the peripheral surface of the windshield is an uppermost peripheral surface of the windshield.

7. The vehicular windshield apparatus of claim 1, wherein the diffraction grating pattern protrudes from the surface of the predetermined portion of the windshield towards eyes of the driver.

8. The vehicular windshield apparatus of claim 7, wherein a height of the diffraction grating pattern from the surface of the windshield is greater than 0 and less than 10 μm.

* * * * *